(12) United States Patent
Brown et al.

(10) Patent No.: US 9,101,345 B2
(45) Date of Patent: Aug. 11, 2015

(54) SURGICAL GUIDE AND TISSUE ANCHOR

(75) Inventors: Stuart Ian Brown, Fife (GB); Stuart Coleman, Dundee (GB); Alfred Cuschieri, Fife (GB); Leslie Kelly, Fife (GB); Paul Simon Maher, Galway (IE); James Duncan Shaw Martin, Dundee (GB)

(73) Assignee: The University of Dundee, Dundee (GB)

( * ) Notice: Subject to any disclaimer, the term of this patent is extended or adjusted under 35 U.S.C. 154(b) by 549 days.

(21) Appl. No.: 13/354,061

(22) Filed: Jan. 19, 2012

(65) Prior Publication Data

US 2012/0245598 A1    Sep. 27, 2012

(30) Foreign Application Priority Data

Jan. 19, 2011    (GB) .................................. 1100902.4

(51) Int. Cl.
| | | |
|---|---|---|
| *A61B 17/03* | (2006.01) | |
| *A61B 17/02* | (2006.01) | |
| *A61B 17/04* | (2006.01) | |
| *A61B 17/122* | (2006.01) | |
| *A61B 17/128* | (2006.01) | |
| *A61B 17/00* | (2006.01) | |
| *A61B 17/28* | (2006.01) | |
| *A61B 17/29* | (2006.01) | |

(52) U.S. Cl.
CPC ......... *A61B 17/0218* (2013.01); *A61B 17/0401* (2013.01); *A61B 17/1227* (2013.01); *A61B 17/1285* (2013.01); *A61B 2017/00473* (2013.01); *A61B 2017/00951* (2013.01); *A61B 2017/0404* (2013.01); *A61B 2017/0464* (2013.01); *A61B 2017/2808* (2013.01); *A61B 2017/2931* (2013.01); *A61B 2017/2948* (2013.01)

(58) Field of Classification Search
CPC ........... A61B 17/0218; A61B 17/0401; A61B 17/1227; A61B 17/1285
USPC ......... 606/139–148, 151, 157, 158, 184, 185; 604/174; 24/3.11
See application file for complete search history.

(56) References Cited

U.S. PATENT DOCUMENTS

| | | | | |
|---|---|---|---|---|
| 3,332,439 | A * | 7/1967 | Burke ........................... | 137/556 |
| 3,822,052 | A * | 7/1974 | Lange .............................. | 251/10 |
| 3,882,854 | A * | 5/1975 | Hulka et al. .................. | 600/104 |
| 4,112,951 | A * | 9/1978 | Hulka et al. .................. | 128/831 |
| 4,535,773 | A * | 8/1985 | Yoon ............................. | 606/185 |
| 4,596,249 | A * | 6/1986 | Freda et al. .................... | 606/145 |
| 5,304,183 | A * | 4/1994 | Gourlay et al. ............... | 606/142 |
| 5,391,156 | A * | 2/1995 | Hildwein et al. ............. | 604/174 |
| 6,814,742 | B2 * | 11/2004 | Kimura et al. ................ | 606/151 |
| 7,037,307 | B2 * | 5/2006 | Dennis ............................ | 606/47 |
| 7,828,775 | B2 * | 11/2010 | Okoniewski ............. | 604/167.01 |
| 8,647,350 | B2 * | 2/2014 | Mohan et al. ................. | 606/139 |
| 2009/0222029 | A1 * | 9/2009 | Gordin et al. ................. | 606/151 |
| 2009/0259184 | A1 * | 10/2009 | Okoniewski ............. | 604/165.02 |

\* cited by examiner

*Primary Examiner* — Kathleen Holwerda
(74) *Attorney, Agent, or Firm* — Foley & Lardner LLP

(57) ABSTRACT

A surgical tissue anchor comprising a plurality of jaws suitable for clamping onto tissue, clamp component(s) operable to bias the jaws in a closed position and attachment structure operable for attachment of the anchor to one or more tethers for retracting the clamped tissue. The one or more tethers are guided to the desired region using a surgical guide.

24 Claims, 11 Drawing Sheets

SURGICAL GUIDE AND TISSUE ANCHOR

TECHNICAL FIELD

The present invention relates to a surgical guide and tissue anchor and particularly to apparatus for tethering and retracting tissues during surgery, in particular minimal access surgery.

BACKGROUND

During surgery, surgeons need to move (retract) tissues to facilitate access and/or other surgical tasks. Retraction is a critical aspect of all forms of surgery, but particularly minimal access surgery (MAS), where the operating space is limited and the instruments are fed through the abdominal wall via special ports. Normally one of the access ports is dedicated to a retraction instrument and, in normal procedures, an assistant surgeon is required to hold the retraction instrument. While MAS is undoubtedly less traumatic than open surgery, it remains desirable to use as few access wounds as possible.

The demand for a new retraction system is most apparent in the rapidly developing fields of single port laparoscopic surgery (SPLS) and natural orifice surgery. Here, the use of a single small access wound severely limits the number of instruments that can be effectively inserted. In order to ensure optimal utilisation of space within the restricted space offered by the single access port, it is desirable that retraction for these types of surgery should be effected without using the port.

It is known that surgeons have retracted tissue in the above context by suturing between the tissue and the abdominal wall. This is achieved by taking a suture and thread into the abdominal space either via a port or by penetrating the abdominal wall with the suture needle.

Retracting organs using chord-like elements is known. For example, the retraction of hollow organs (arteries, veins, oesophagus) with elastomeric slings is routine in many operations. Similarly, hitching the fundus of the gall bladder to the abdominal wall by percutaneous sutures, introduced many years ago by A Cuschieri, has been used, but for full exposure of the gallbladder for SPLS-cholecystectomy two tethering percutaneous sutures (occasionally three) are needed, at right angles to each other: one to lift the gallbladder and liver anteriorly, and the other to stretch the cystohepatic triangle to the right, thus providing the necessary exposure for safe dissection of the cystic artery and cystic duct, both of which require clipping and division for detachment of the gallbladder from the biliary tract. The precise insertion of these sutures is technically demanding and time consuming. However, their use in SPLS-cholecystectomy serves to confirm that tethering techniques provide effective retraction and surgical exposure of the operative field.

The applicants have identified several problems with using conventional internal or percutanous sutures for laparoscopic exposure of organs: passage of atraumatic sutures (on straight needles) through the abdominal wall can be difficult; the needle has to be reversed, after passage through the gallbladder, in the peritoneal cavity and tied to, or inserted through, the abdominal wall from inside out (in the case of external suture tethers) and the mechanical loads on the tissues from the suture tension are high, resulting in tearing and leakage of, for example, bile. Moreover, the technique is laborious and time consuming especially as usually two and sometimes three suture tethers are needed. Once in place, the direction of pull of suture tethers cannot be changed.

SUMMARY

According to a first aspect of the present invention there is provided a surgical tissue anchor comprising a plurality of jaws suitable for clamping onto tissue, clamping means operable to bias the jaws in a closed position and attachment means operable for attachment of the anchor to one or more tethers for retracting the clamped tissue.

Advantageously, a first jaw, of the pair of jaws, comprises a first facing surface and the second jaw comprises a second facing surface and wherein the first facing surface has tissue piercing means extending therefrom towards the second facing surface and the second facing surface comprises a receiving hole disposed suitably therein to receive the tissue piercing means when the anchor is in its normally closed state.

The tissue piercing means is advantageously a needle. The needle is preferably a straight tapered round bodied needle of between 2 mm and 3 mm in length and between 0.5 mm and 1.5 mm in diameter, and more preferably 2.6 mm in length and 0.8 mm in diameter.

The first and second surface are advantageously profiled to cooperate with each other, in the normally closed state, to provide a seal therebetween.

The clamping means preferably comprises a biasing spring operable to provide a biasing force on the jaws to urge the jaws into a normally closed state.

The surgical tissue anchor may further comprise a mechanical actuator having a spring pin and operable to translate a force, applied to the spring pin, substantially in the direction of the longitudinal axis thereof, into a force to separate the jaws.

The attachment means may be disposed on the spring pin.

The attachment means may be disposed on a peripheral portion of the spring pin.

The attachment means preferably comprises an attachment aperture.

The attachment means advantageously further comprises a mechanical actuator attachment aperture, extending through the mechanical actuator, and a pair of diametrically opposed housing apertures, extending through a covering housing, wherein the mechanical actuator aperture and the housing aperture are axially aligned to form a single attachment aperture.

The mechanical actuator aperture is advantageously oval in shape.

The surgical tissue anchor advantageously further comprises an applicator for remotely clamping the anchor to tissue.

The applicator may comprise attachment means operable to detachably attach the applicator to the attachment means of the anchor.

The applicator attachment means preferably comprises a hook-shaped connector.

The applicator may comprise an actuator rod connected to an actuator handle, the actuator handle being operable to move the actuator rod in a direction along its longitudinal axis.

Movement of the actuator rod in a direction along its longitudinal axis advantageously causes the jaws of the anchor to separate.

The surgical anchor may further comprise a tissue opening in which tissue adjacent the closed jaws is gathered and disposed when the anchor is closed.

According to a second aspect of the present invention a surgical tethering and retraction kit comprises a surgical guide and one or more surgical tissue anchors according to the first embodiment of the present invention.

The surgical guide advantageously comprises a handle portion, a tubular guide member, extending from the handle portion, and a tether, wherein the tether comprises an attachment tag disposed thereon.

The tubular guide is preferably a needle.

The tubular guide is preferably adjustable in length.

The tubular guide may be telescopic.

The surgical guide may further comprise a tether clamp operable to clamp the tether at a desired length.

The tether clamp may be a spring biased clamp.

Alternatively, or additionally, the tether clamp may be a screw clamp.

The surgical guide advantageously further comprises an inner sleeve disposed within the tubular guide, coaxially therewith.

The inner sleeve is advantageously extendible in the direction of its longitudinal axis such that it can be exposed beyond the distal end of the tubular guide.

The inner sleeve is advantageously biased by a spring attached thereto, the spring being disposed in the handle portion.

The inner sleeve advantageously comprises an aperture disposed at, or adjacent to, its distal end, through which the tether can be extended.

The surgical guide may further comprises a retaining flange suitably disposed and operable to rest on the skin of the animal or human body and thereby cover the incision through which the guide extends.

The tag may comprise a short, straight, rigid rod-like component, attachable to the tether at its midpoint such that it is inclined, when not constrained by the guide, to form an angle of between 45° and 135° to the tether and, more preferably, to form an angle of approximately 90° to the tether.

Alternatively, the tether may comprise a hook formed at or near the distal end of the tether.

Alternatively or additionally, the guide comprises a channel positioned on the outer surface of the guide such that a tether can extend along the channel when being deployed.

The guide may further comprise a collar which extends into the human or animal body to prevent contact between the incision and the tether.

The collar protects the tissue, which forms the puncture wound, from damage which might otherwise be caused by the 'sawing' action of the tether as it moves back and forth.

The collar may be part of the retaining piece or alternatively at least part of the collar may be part of the guide.

Optionally the collar and guide form a single piece wherein the guide is retractable into the collar.

The retaining piece may comprise a plate which abuts against the outer surface of the body.

The retaining piece preferably comprises a flange.

The guide preferably further comprises means for facilitating movement thereof such that, in use, the orientation of the apparatus can be adjusted.

The means for facilitating movement is preferably disposed on the retaining piece.

Optionally, the attachment means may provide a fixed attachment between the tether and the anchor. In this case, the tether is fixed to the anchor and removal of the tether from the site of the surgical procedure is by cutting the tether external to the body cavity and removing the remaining portion with the anchor.

Alternatively, the attachment means may comprise a barb and a barb receiving catch operable to receive the barb and form a fixed connection therebetween.

Optionally, the connection means is formed by an adhesive coupling between the tether and the anchor.

The tether is preferably non-rigid and is made from thread or surgical suture.

In accordance with a second aspect of the invention there is provided, the use of an apparatus in accordance with the first aspect of the invention for retracting and/or tethering tissue inside a human or animal body at the site of a surgical procedure.

BRIEF DESCRIPTION OF THE DRAWINGS

The present invention will now be described by way of example only with reference to the accompanying drawings in which.

DETAILED DESCRIPTION OF THE ILLUSTRATED EMBODIMENTS

The present invention concerns apparatus and methods for retracting and/or tethering tissue in operations where an internal operating space has been created, for example by inflation of the peritoneum.

The invention uses an anchor attached to the tissue, a retaining piece deployed outside the patient, connected to a guide and a tether linking the anchor to the retaining piece. Such a system of components can provide excellent exposure, be easy to deploy and be adjusted at will. The system invention may also assist in retracting tissue without causing damage to the abdominal wall or internal organs. The system may use thread as a tether but avoids the difficult suturing process by using the anchor/tether coupling.

Advantageously, the illustrated apparatus and method will provide tethered exposure of an area where a surgical procedure is to be performed quickly and with relative ease. Furthermore the retraction direction can be altered/adjusted expeditiously during the operation using means for facilitating movement thereof such that, in use, the orientation of the apparatus can be adjusted. The means for facilitating movement is may be disposed on the retaining piece and may, for example, be a handle or the like.

Figures 1A, 1B:
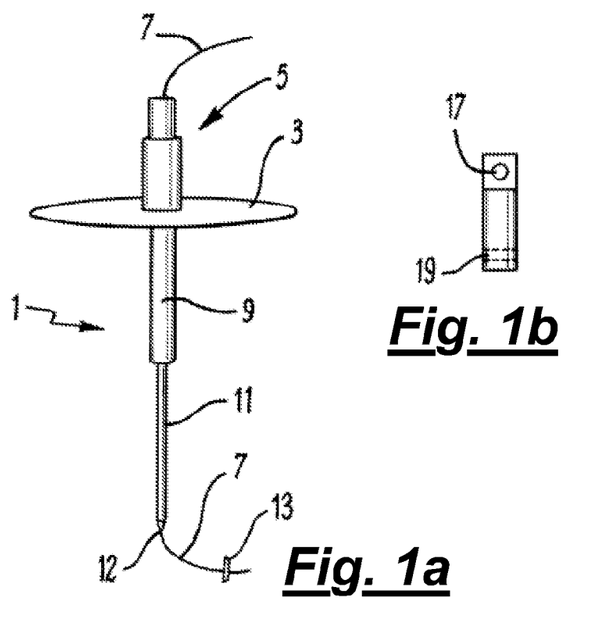
FIG. 1a is a side elevation of a first embodiment of an apparatus constructed in accordance with the present invention, without the anchor.
FIG. 1b is a front elevation of an example of an anchor in accordance with the present invention and FIG. 1c is a side elevation of the anchor.
Figure 1C:
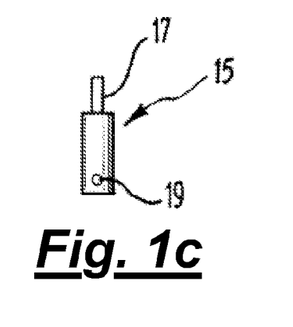

Referring to FIGS. 1a-1c, there is shown a apparatus 1 that optionally comprises a retaining piece 3 which rests upon the skin of the patient and is connected to a holder 5 which releaseably holds in place a tether 7. In this embodiment, the holder has a mechanical clamp (not shown) which securely holds the tether in position but can also be released to allow the length of the tether to be adjusted. A collar 9 extends downwards from the retaining piece 3 on the side of the retaining piece remote from the holder 5. The collar 9 is sized to be in contact with, for example, the incision in the abdominal wall of the patient, to prevent direct contact between the abdominal wall and the tether 7, when the apparatus is in use.

A guide 11 extends from the collar 9 away from the retaining piece 3 and the holder 5. In this example, the guide comprises a hollow needle through which the tether 7 passes in order to be positioned at the site where the surgical procedure is to be carried out. The needle can also be used to create the access point to the site of the surgical procedure. In FIG. 1a, the tether 7 extends out from the point of the needle. Referring to FIG. 1b and FIG. 1c, a loop 17 through which the end of the tether can be threaded is shown along with a fixing point 19 which connects the anchor 15 to body tissue. A tag 13 is provided on the tether 7 to assist with attaching the tether to the loop 17 of the anchor 15. In a preferred embodiment the collar 9 and the guide 11 are extendable and retractable in the direction of the longitudinal axis thereof to optimise the desired positioning of the tether and anchor and facilitate the procedure.

Figures 2A, 2B:
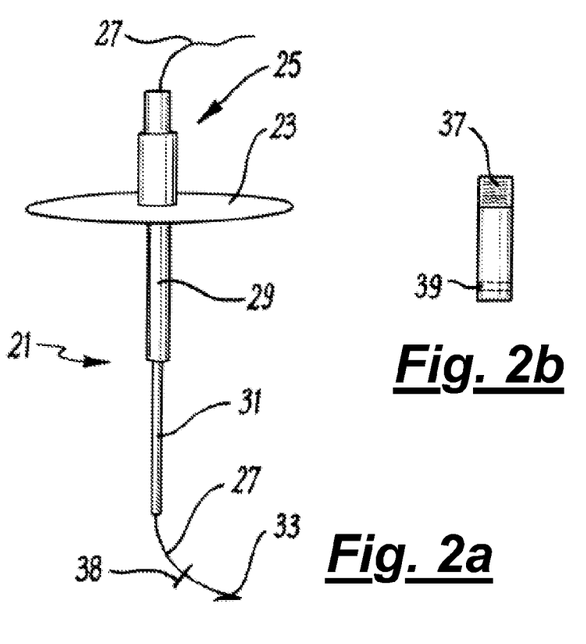
FIG. 2a is a side elevation of a second embodiment of an apparatus constructed in accordance with the present invention, without the anchor.
FIG. 2b is a front elevation of an example of an anchor in accordance with the present invention and FIG. 2c is a side elevation of the anchor.
Figure 2C:
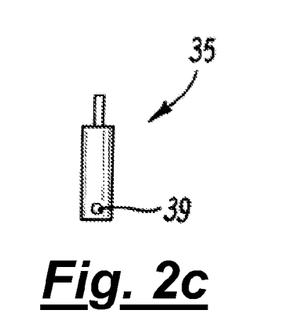

FIGS. 2a to 2c show a second embodiment of the present invention. The apparatus 21 comprises a retaining piece 23 which rests upon the skin of the patient and is connected to a holder 25 which releaseably holds in place a tether 27. In this embodiment, the holder has a reel or other suitable device which securely holds the tether in position but can also be released to allow the length of the tether to be adjusted. The collar 29 extends downwards from the retaining piece 23 on the side of the retaining piece remote from the holder 25. In this example, the collar 29 is sized to be in contact with, for example, the abdominal wall of the patient, to prevent direct contact between the abdominal wall and the tether 27, when the apparatus is in use.

A guide 31 extends from the collar 29 away from the retaining piece 23 and the holder 25. In this example, the guide comprises a hollow conduit 31 through which the tether 27 passes in order to be positioned at the site where the surgical procedure is to be carried out. A separate puncture wound is made to allow the conduit 31 to be introduced to the site of the surgical procedure. The puncture wound is made by insertion of guide 31, which is preferably in the form of a needle. Having only an puncture wound, as opposed to an incision, is advantageous as it significantly reduces the risk, pain and recovery time which the patient experiences. In FIG. 2a, the tether 27 extends out from the point of the conduit 31. A front elevation and a side elevation of an anchor 35 are shown in FIGS. 2b and 2c. The anchor 35 comprises an attachment area 37 at the end thereof to which an adhesive may be applied and to which the tether end 33 can thereby be securely fixed. The tether end 33 may be flattened or otherwise conveniently shaped to improve the bond between the anchor 35 and the tether 27. A fixing point 39 is operable to connect the anchor 35 to body tissue. A tag 38 is provided on the tether 27 to assist with attaching the tether to the fixing point 39 of the anchor 35.

In this embodiment, the bonding between the tether 27 and the anchor 35 is substantially permanent, when the surgical procedure has ended, the tether may be cut and removed along with the anchor.

Figure 3:
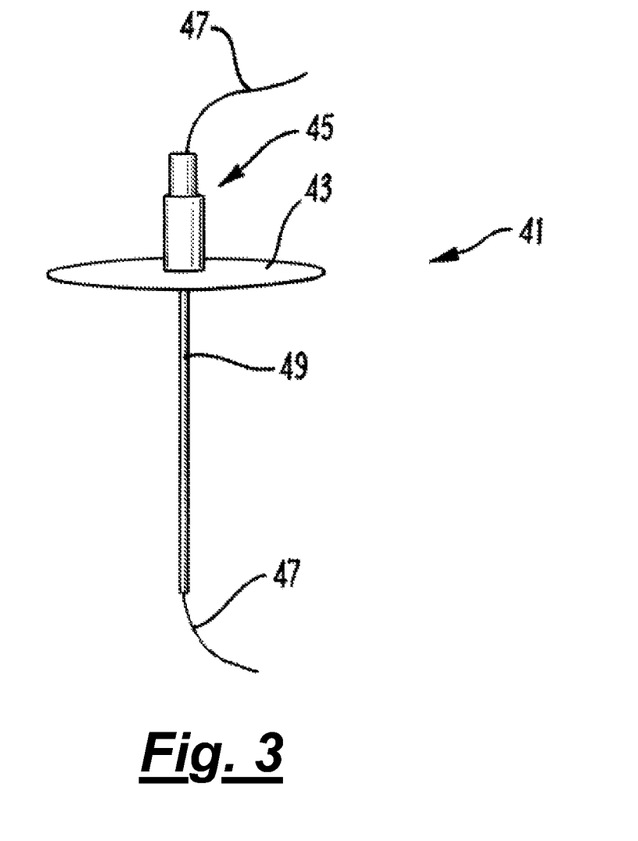
FIG. 3 is a side elevation of a third embodiment of an apparatus constructed in accordance with the present invention.

FIG. 3 shows another embodiment which has similar features to those of FIGS. 1a and 2a and may further comprise either the anchor of FIGS. 1b and 1c, or FIGS. 2b and 2c. The apparatus 41 comprises a retaining piece 43 a holder 45 a tether 47 and a guide 49. This embodiment does not have a collar as it is used in procedures in which the type of tether and/or the surgical procedure in question does not pose a risk of friction damage to the area around the incision.

Figure 4:
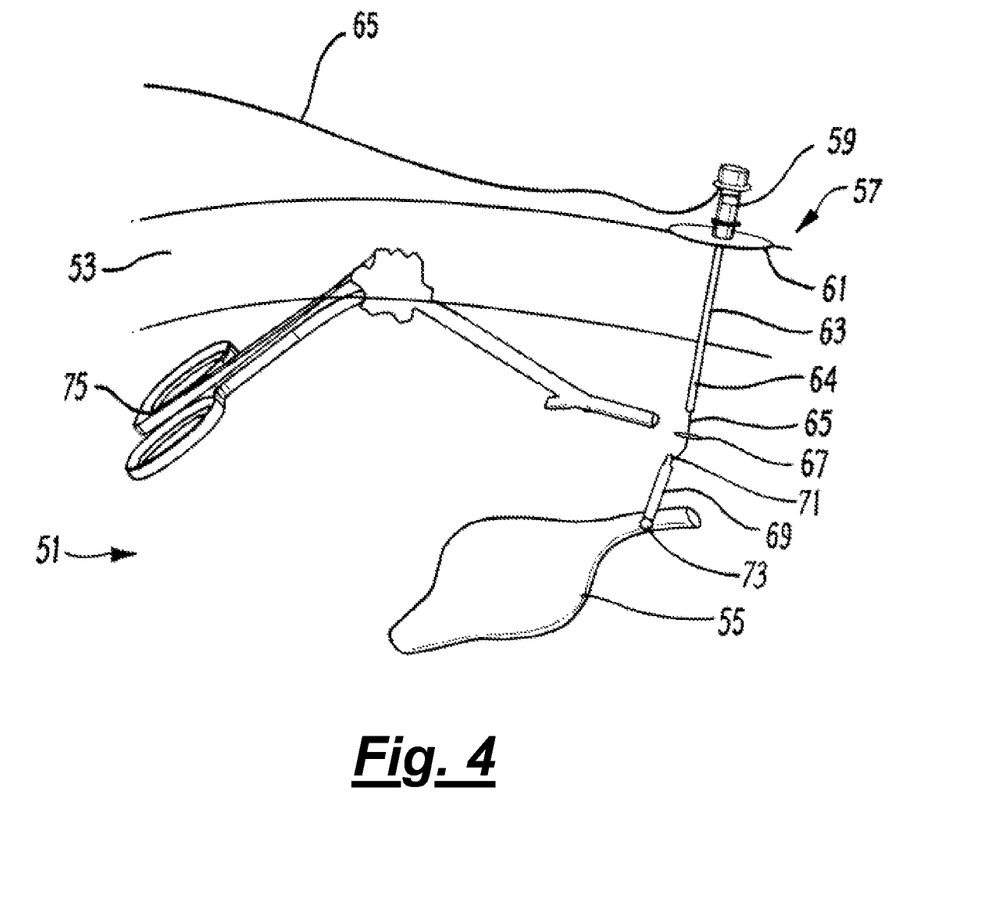
FIG. 4 shows the introduction and connection of the apparatus of the first embodiment of the present invention at the site of a surgical procedure.

FIG. 4 shows the introduction and use of the illustrated apparatus. A surgical site 51 is bounded by the abdominal wall 53, through which the surgical instruments are introduced in a laparoscopic procedure which requires the gall bladder 55 to be tethered and retracted. The guide, in the form of a needle 64, is passed through the abdominal wall 53 with the collar 63 in contact with the sides of the incision in the abdominal wall 53. The tether 65 may be provided with a tag 67. The tether 65 and tag 67 is fed out from the end of the needle 64 through an inner sleeve, which is telescopically extended out from the end of the needle 64. Connection of the anchor to the tether, which may be stored in the needle until ready for use, is accomplished by passing the tag 67 through the loop 71 on the anchor 69. To align the tag 67 with the anchor 69 the surgeon may manipulate the anchor with a laparoscopic instrument, or the holding piece and needle by hand, whichever is found to be easier. Alternatively, the loop may be slid up the guide before extruding the tether and its tag out of their resting position inside the guide. As the anchor is then moved to its site it becomes caught on the tether.

Once the tether 65 is attached to the anchor 69, the needle 64 is withdrawn such that the collar 63 extends around the tether through the abdominal wall 53. The tether 65 can be retracted by pulling it from the outside of the patient in order to move/retract the gall bladder 55.

In an alternative embodiment the guide (needle) may be of a length to suit the patient's abdominal wall thickness, in which case the guide (needle) would not need to be withdrawn.

When retraction is no longer required the tether is cut and the tag is removed along with the anchor.

Figure 5:
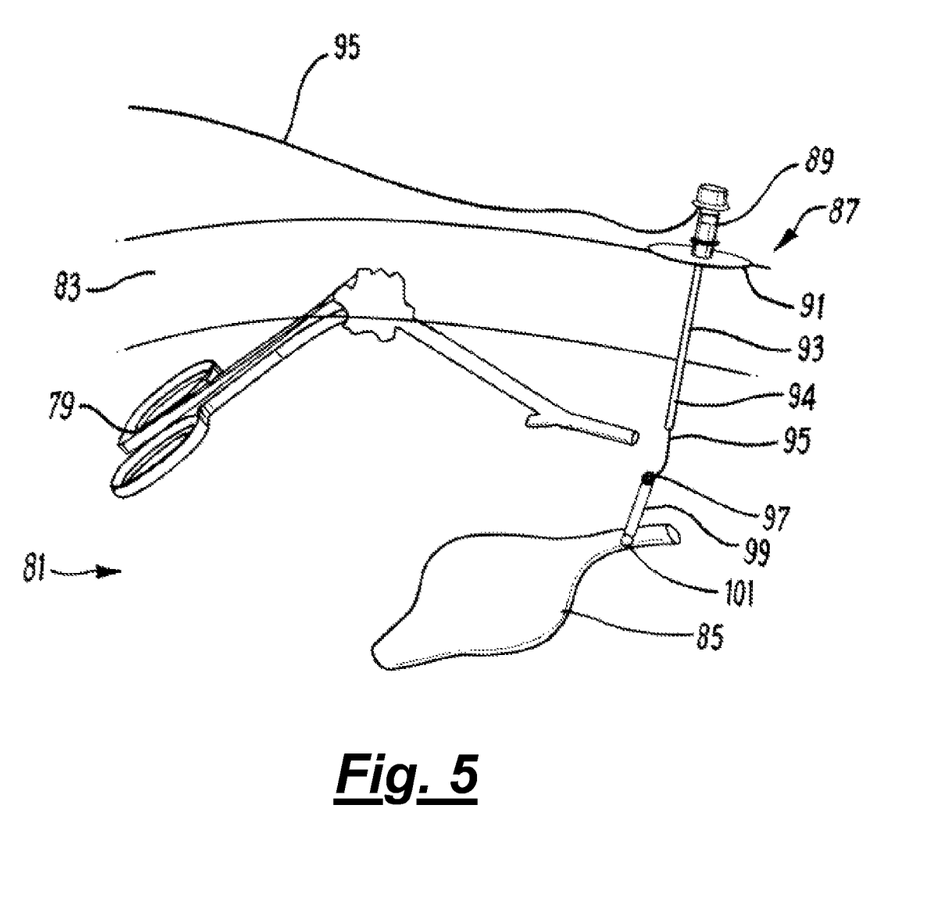
FIG. 5 shows the introduction and connection of the apparatus of second embodiment of the present invention at the site of a surgical procedure.

FIG. 5 shows another example of the introduction and use of the illustrated apparatus. The surgical site 81 is bounded by the abdominal wall 83, through which the surgical instruments are introduced in a laparoscopic procedure which requires the gall bladder 85 to be tethered and retracted. The needle 94 is passed through the abdominal wall 83 with the collar 93 in contact with the sides of the incision in the abdominal wall 83. In this embodiment, an adhesive is applied to the end of the tether and/or a connecting area 97 on the anchor 99 and the laparoscopic instrument 79 is used to connect the tether 95 to the anchor 99. As previously described, this connection is substantially permanent, when the surgical procedure has ended, the tether may be cut and removed along with the anchor.

Once the tether 95 is attached to the anchor 99, the needle 94 is withdrawn such that the collar 93 extends around the tether through the abdominal wall 83. The tether 95 can be retracted by pulling it from the outside of the patient in order to move/retract the gall bladder.

Figure 6:
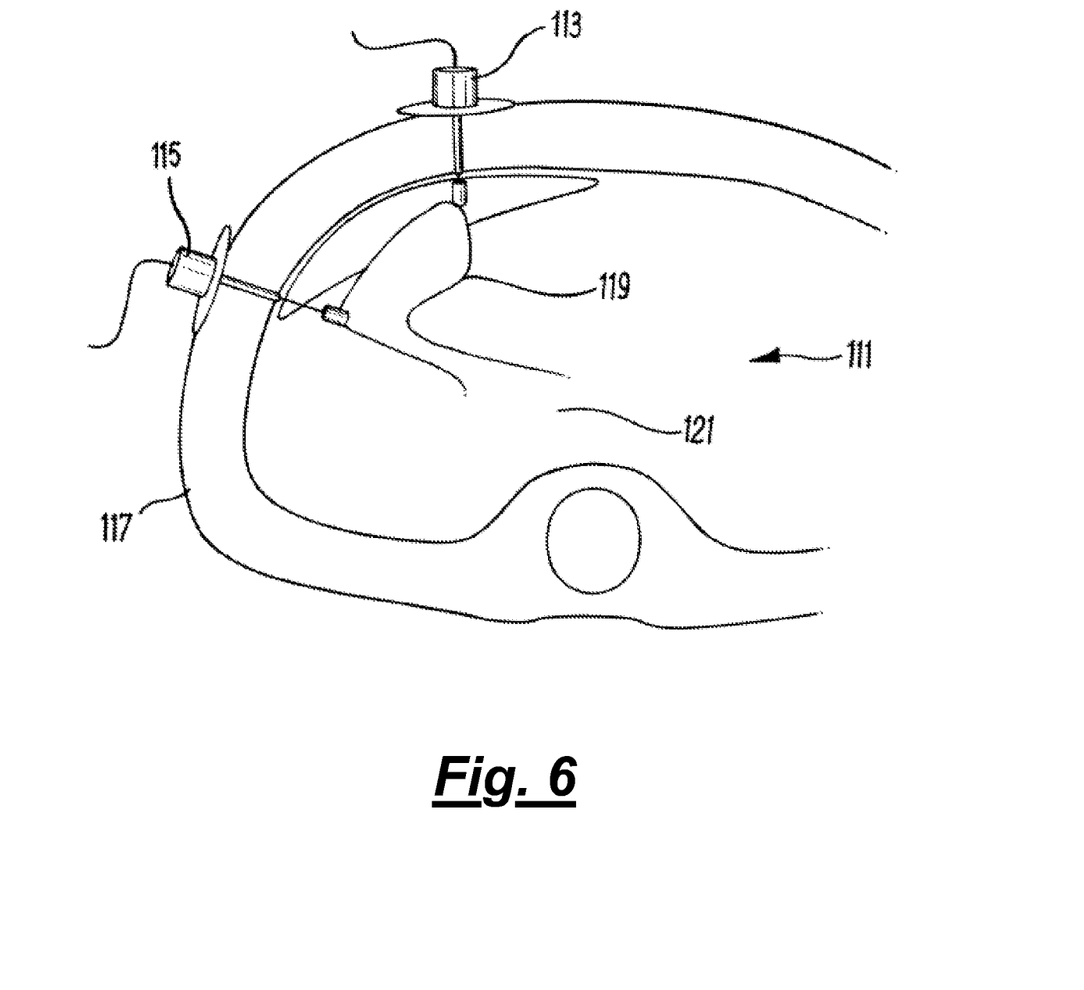
FIG. 6 shows an example of an apparatus constructed in accordance with the present invention, in use.

The retraction concept is further illustrated in FIG. 6 which shows a surgical site 111 along with a first apparatus 113 and a second apparatus which extend through the abdominal wall and are used to retract the gall bladder 119 to allow better surgical access to the cystohepatic triangle 121.

As indicated above, the anchor is delivered on a simple laparoscopic introducer and attached to the target organ (i.e. the gall bladder). It should be noted that embodiments of the anchor which have piercing means cannot be subsequently released and moved once they have been clamped onto the tissue. In practice, using an anchor having piercing means necessarily assumes that the pierced organ will be removed at the end of surgery. Obtaining the correct retracted position is then a matter of adjusting the tension in the tether with a simple external control. The system is easy to use and safe. The actions described above are basic manipulations which any laparoscopic surgeon can perform. Once the tether and anchor are connected the needle is withdrawn, eliminating one potential source of iatrogenic injury.

It will be appreciated that alternative embodiments of the anchor may not have piercing means and may simply rely on the clamping force of the anchor.

The illustrated embodiments may reduce the risk of entanglement in the tether(s), by having only a short tensioned section of the tether remaining in the intraperitoneal cavity: the tether is withdrawn largely or entirely into a flexible tube of the holding piece. In addition, any length of tether exposed in the abdominal space will be under tension. While two and occasionally three tethers will be employed, the use of the tethers under tension will minimise the presence of extensive loops of loose tether material being present in the peritoneal cavity.

It will be appreciated that other configurations of tether and anchor may be used in surgical procedures and the disclosed apparatus is equally applicable to such alternative configurations, such as, for example: the anchor may be connected to a retaining piece secured inside the abdomen, perhaps to another anchor, or a single retainer may be secured a plurality of tethers and/or anchors and/or a plurality of anchors may be secured on a single tether. The disclosed apparatus according to the present invention is applicable to these configurations and the application should be construed accordingly.

The surgeon will have a choice of anchors from a range to be offered with the system depending on the thickness and consistency of the target organ. However, a preferred novel anchor is shown in FIG. 7 and described below.

Figure 7:
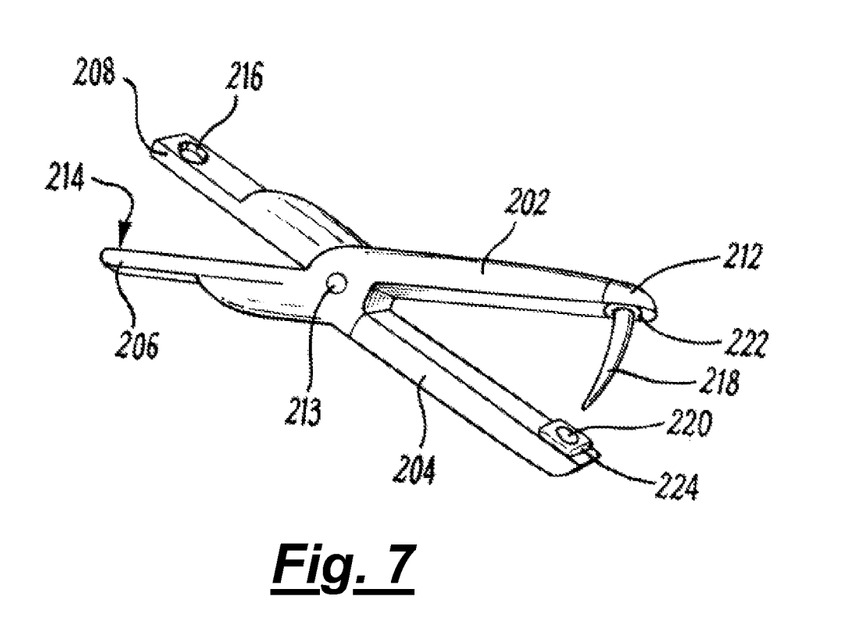
FIG. 7 is a drawing of an anchor, according to the present invention, suitable for use with the apparatus of the invention of FIGS. 1, 2 and 3.

Referring to FIG. 7, there is shown an anchor 200 suitable for use with the apparatus of FIGS. 1, 2 and 3. Anchor 200 comprises a first member 202 and a second member 204, each member having a tether attachment end, 206 and 208, respectively, and a tissue attachment end, 210 and 212, respectively. The first and second members, 202 and 204, are pivotably attached to each other by a pivot 213 disposed substantially intermediate the tether attachment ends, 206 and 208, and the tissue attachment ends, 210 and 212, such that the first and second members, 202 and 204, are operable to pivot relative to each other.

In pivoting the first and second members, 202 and 204, relative to each other, the first and second tissue attachment ends, 210 and 212, act as jaws, whereby the first and second members are in a closed position when they pivoted towards each other and an open position when pivoted away from each other.

Each of the tether attachment ends, 206 and 208, has attachment means, 214 and 216, respectively for attaching a tether. The embodiment shown in FIG. 7 has attachment means comprising apertures (or loops). However, it will be appreciated that other attachment means may be used within the working of the anchor as hereinbefore described.

The first tissue attachment end 212 has a piercing member 218 extending therefrom in the direction of the second tissue attachment end. In a preferred embodiment the piercing member is advantageously curved to correspond with the arcuate nature of the pivoting action.

The second tissue attachment end 214 has a receiving hole 220 (or aperture) disposed thereon to face and, in use, receive the piercing member 218 when the first and second members are pivoted towards each other into the closed position.

The first tissue attachment end 212 further comprises an annular groove 222 surrounding the point at which the piercing member 218 extends therefrom.

The second tissue attachment end 214 further comprises a raised annular lip 224 disposed and dimensioned to cooperate with the annular groove 222, in a male-female connection, when the anchor is in the closed position such that the accuracy and certainty is provided in relation to the relative positions of the first and second tissue attachment ends and wherein a seal is created between the first tissue attachment end 212 and the second tissue attachment end 214 thereby preventing leakage of fluid from the tissue, such as, for example, bile.

Figure 11:
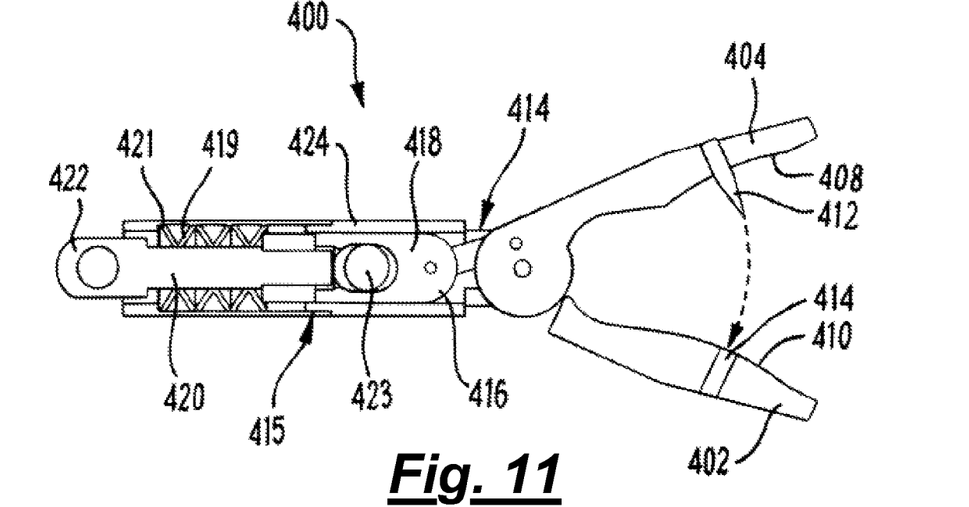
FIG. 11 is a part cross section of a preferred embodiment of a surgical tissue anchor according to the present invention.
Figure 12:
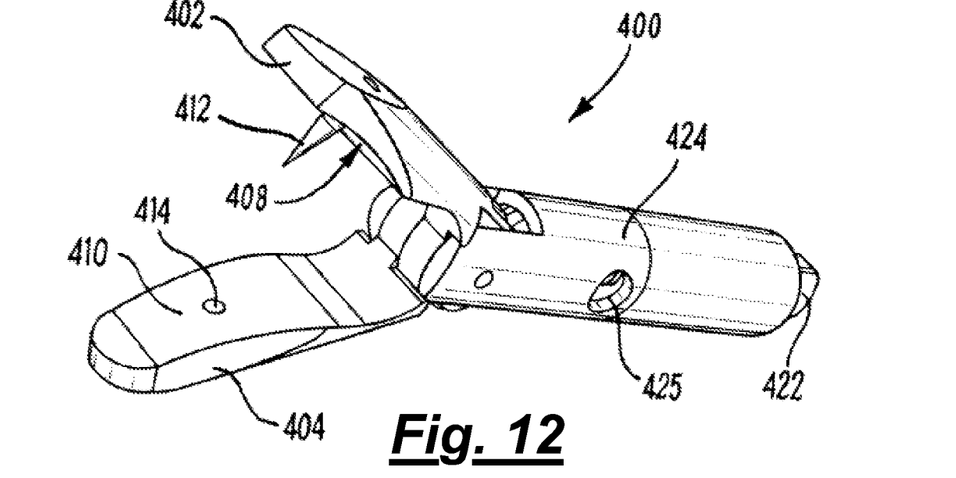
FIG. 12 is a drawing showing an alternative view of the surgical tissue anchor of FIG. 11.

A seal may be alternatively created by the opposing surfaces, of the first tissue attachment end 212 and the second tissue attachment end 214, being of a cooperating concave and convex profiles which when abutted against each other form a fluid seal. This is shown in FIGS. 11 and 12 as a preferred embodiment.

In use, in the open position, the first and second tissue attachment ends are positioned such that a target tissue, such as, for example, the gall bladder, is disposed therebetween. The first and second members are then pivoted relative to each other such that the anchor is pivoted into the closed position. In doing so, the piercing member 218 punctures the target tissue and, upon complete closure of the members, the corresponding groove 220 and lip 222 form a seal around the puncture wound to prevent the leakage of fluids.

The anchor may be secured in the closed position by means of a ratchet or spring mechanism.

The tether is secured to the anchor using the attachment means 214 and 216.

Figure 8:
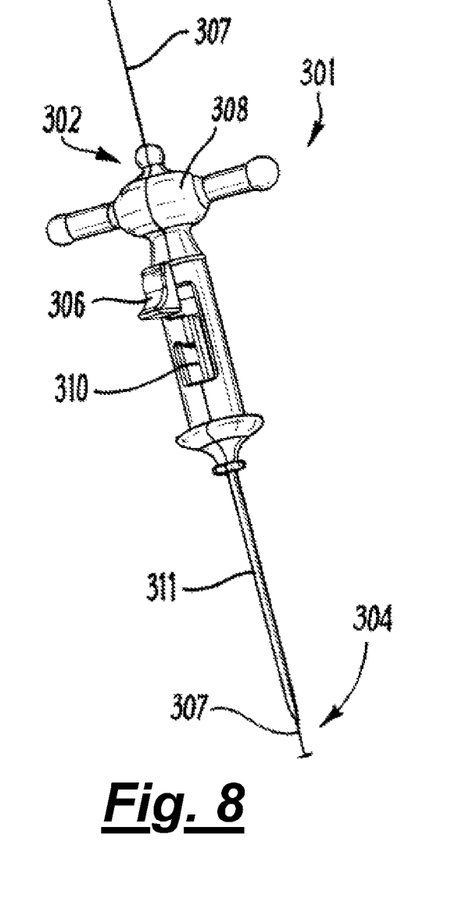
FIG. 8 is a drawing of a preferred embodiment of a surgical guide according to the present invention.
Figure 9:
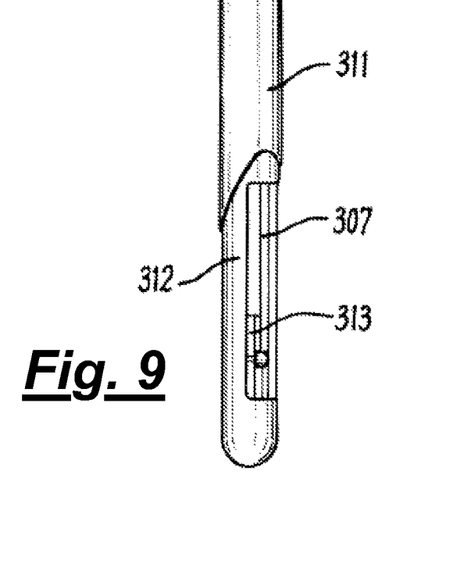
FIG. 9 is a drawing showing a more detailed view of the distal end of the surgical guide of FIG. 8.
Figure 10:
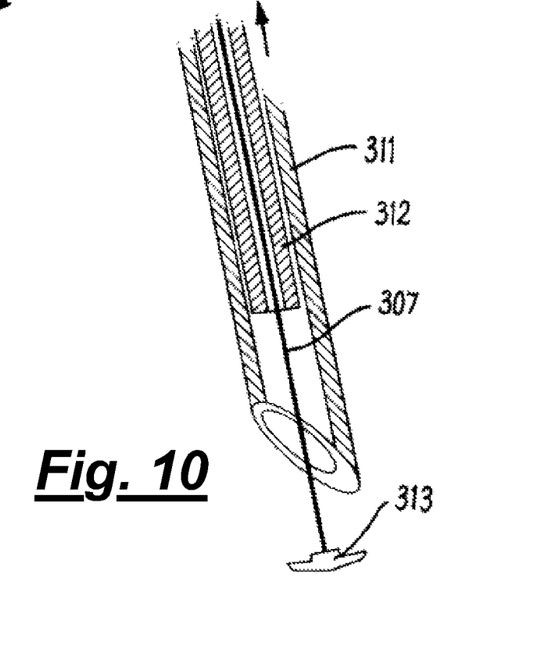
FIG. 10 is a drawing showing a detailed view of the distal end of the surgical guide of FIG. 8, wherein the tether is extending from the guide.

FIGS. 8 to 10 show an embodiment of an apparatus 301 constructed according to the present invention.

The apparatus 301 has a guide 311 for guiding a tether 307 to a predetermined position within the human or animal body, as mentioned above in relation to the previous embodiments. The tether 307 may, for example, be a 0.35 mm diameter monofilament wire.

Referring to FIG. 8, the apparatus 301 has a proximate end 302 and a distal end 304, the proximate end being the end which, in use, is closest to the surgeon. The guide 311 is formed from a tubular member having an internal bore through which the tether 307 extends. The tubular member may be a needle, in which case the guide can also be used to make the initial puncture wound into the patient before the guide is further inserted towards the required predetermined position. The needle may be, for example, a 100 mm long 14 gauge needle (i.e. having a 2.1 mm outer diameter and a 1.78 mm inner diameter). In an alternative embodiment the guide 311 may be extendable in length. For example, the guide may be telescopic.

A mechanical clamp 306 is provided at the proximate end 302. The clamp 306 is of a known type having a housing and a clamping member slidably received within the housing, both the housing and the clamping member suitably sized to freely receive the tether 307. The clamp 306 also having a spring positioned to provide a biasing force on the clamping member to thereby misalign the clamping member aperture and the housing aperture and thereby provide a clamping action between the housing and the clamping member. The clamping action being releasable upon manual depression of the clamping member by the surgeon, such that the housing aperture and clamping member aperture are re-aligned.

In an alternative embodiment the clamp may be of a screw type in which a screw fitting is rotated in a thread to clamp the tether at a desired length.

A handle 308 is formed adjacent to the proximate end 302 of the apparatus, between the clamp 304 and the guide 311. The handle 308 being ergonomically formed to facilitate a grip such that the surgeon can grip the handle 308 with his fingers and operate the clamp 306 with his thumb. The handle 308 has an open-ended bore 310 extending along its longitudinal axis which is positioned to provide a continuation of the bore of the guide 311 and the clamp housing.

Also referring to FIG. 9, an inner sleeve 312 is positioned in the bore of the guide (needle) 311 and is extendible beyond the end thereof. The inner feed sleeve 312 may be, for example, a 16 gauge sleeve, having an outer diameter of 1.63 mm and an inner diameter of 1.32 mm, and is made from a resilient material. The inner feed sleeve functions to facilitate feeding and retrieval of the tether 307, and also protects the tether from being worn away and weakened by the guide. The feed sleeve 312 is connected at the proximate end 302 to the handle 308 using a spring mechanism such that it is moveable in a longitudinal direction along the bore of the guide 311 and is biased into a position in which it is withdrawn into the guide 311.

The tether 307 extends along the length of the guide 311 within the feed sleeve 312 and has an attachment tag 313 fixed to its distal end. The attachment tag 313 being a toggle-like member of approximately 5 mm length and 1.5 mm diameter.

The length of tether 307 and also the control of the attachment tag 313 is undertaken using clamp 306. The tether 307 is fed out from the guide 311 through the sleeve 312, as shown in FIG. 10, by overcoming the bias of the spring mechanism. With the tether 307 and tag 313 having been fed through the sleeve 312, such that they extend beyond the end of the guide 311, the inner sleeve 312 is allowed to return to its biased position within the guide 311.

In use, the tether 307 is attached to an anchor using the tag 313, as described in relation to the previously described embodiments; the anchor being attached to the tissue of the patient.

Referring to FIGS. 11 and 12, a preferred embodiment of an anchor 400 comprises a first member in the form of a first jaw 402 and a second member in the form of a second jaw 404. The first and second jaws, 402 and 404, are pivotably attached to each other by a pivot 406. The first and second jaws 402 and 404 also have complimentarily shaped facing surfaces, 408 and 410, respectively, such that upon closure of the jaws a seal is formed between the jaws. The facing surfaces, 408 and 410, may be, for example, formed having complimentary opposing arcuate or concave and convex profiles.

A piercing member in the form of a needle 412 extends from the facing surface 408, of the first jaw 402, in the direction of the, facing surface 410, of the second jaw 404. The needle 412 may, for example, be a straight tapered, round bodied, needle of approximately 2.6 mm and 0.8 mm diameter.

A receiving hole 414 is formed in the facing surface 410, of the second jaw 404, and suitably dimensioned to receive the needle 412, when the jaws are closed against each other.

The anchor 400 further comprises a mechanical actuator 415 having an articulation link 414, a clevis joint 416, a link joint 418 and a spring pin 420. The link joint 418 has an oval shaped attachment aperture 423 extending therethrough.

The jaws 402 and 404 are attached to the clevis joint 416, such that they are rotatable on the axis of the pin thereof. The jaws are also fixed to the articulation link 414.

The link joint 418 connects the clevis joint 416 to spring pin 420, wherein the spring pin is screwed into the link joint 418.

A spring 419 is disposed co-axially with the spring pin 420 and extends between the link joint 418 and a spring abutment 421.

The anchor 400 is shown in the drawings with its jaws 402 and 404 open—i.e. with the spring in compression. However, in normal use, prior to being clamped to tissue the jaws 402 and 404 are biased in a closed position—i.e. the spring is in extension pushing the link joint 418 and clevis joint 416 forward thereby closing the jaws 402 and 404.

Attachment means in the form of an attachment aperture 422 is disposed on the end of the spring pin 420.

Referring to FIG. 12, the anchor 400 is shown with a covering housing 424, which is disposed co-axially with the mechanical actuator 415 such that it covers and houses the mechanical actuator 415 therein. A pair of diametrically opposed attachment apertures 425 (only one shown) extend through the wall of the covering housing 424. The covering housing 424 is positioned relative to the mechanical actuator 415 such that the oval shaped attachment aperture 423 and the housing attachment apertures 425 are axially aligned.

The oval shape of the attachment aperture 423 provides for the continuation of an aperture through the housing apertures 425 as the actuating mechanism 425 moves within the covering housing 424 in the direction of the longitudinal axis of the anchor 400.

Both attachment apertures 422 and 425 are operable to receive a tether passed therethrough and thereby provide an option for the surgeon—i.e. as to how the tether is attached to the anchor. A tether may be attached only to attachment aperture 422 or only to attachment aperture 425. Alternatively, a separate tether may be attached to one of the apertures 422 or 425, thereby providing more control of the direction in which the tissue is retracted.

Figure 13A:
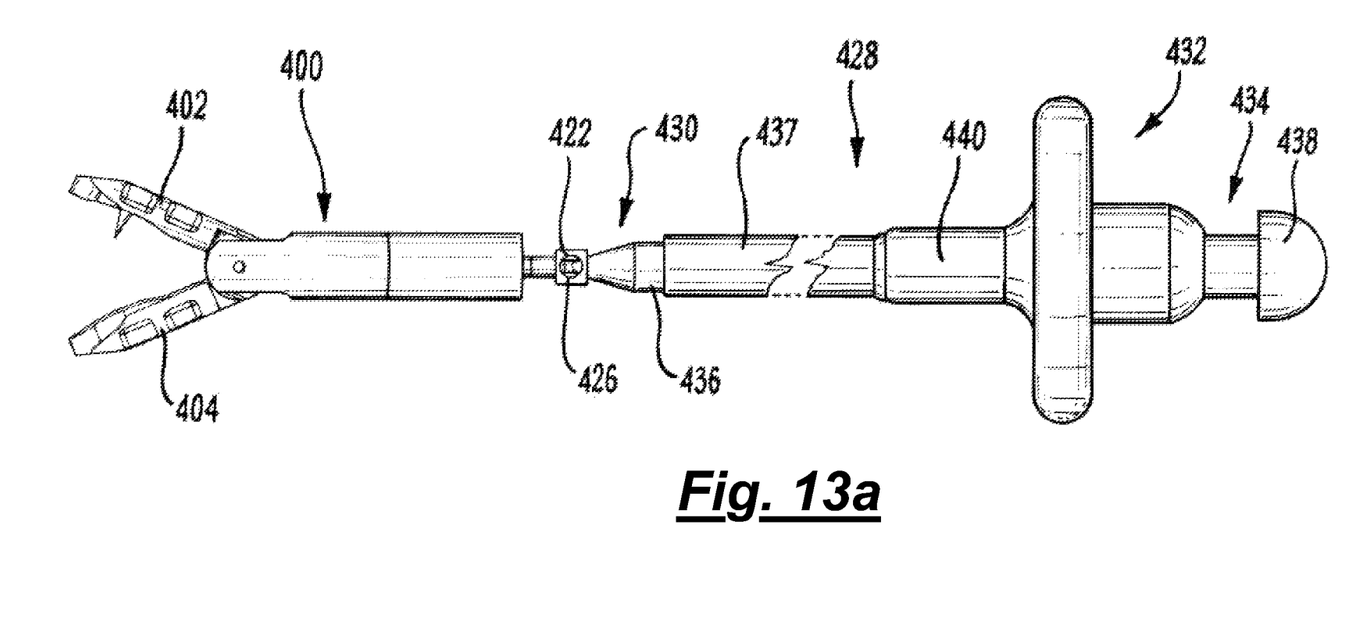
FIG. 13a is a drawing showing the surgical tissue anchor of FIG. 11 and an applicator.
Figure 13B:
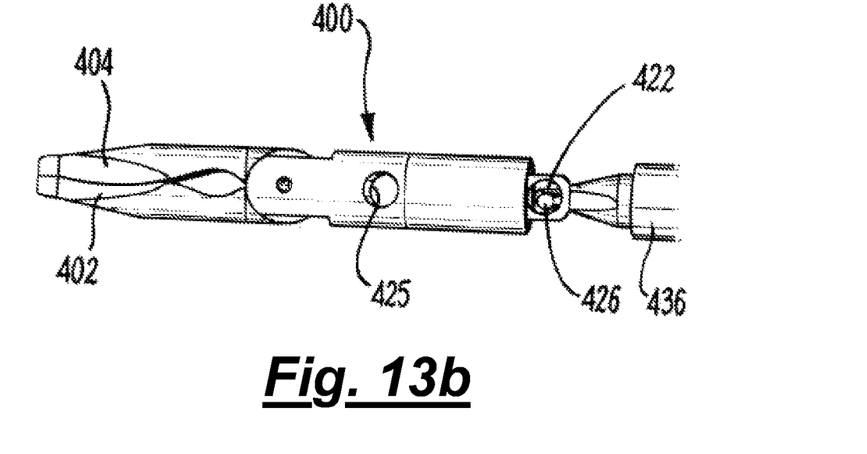
FIG. 13b is a drawing of the anchor and applicator of FIG. 13a in a first position.
Figure 13C:
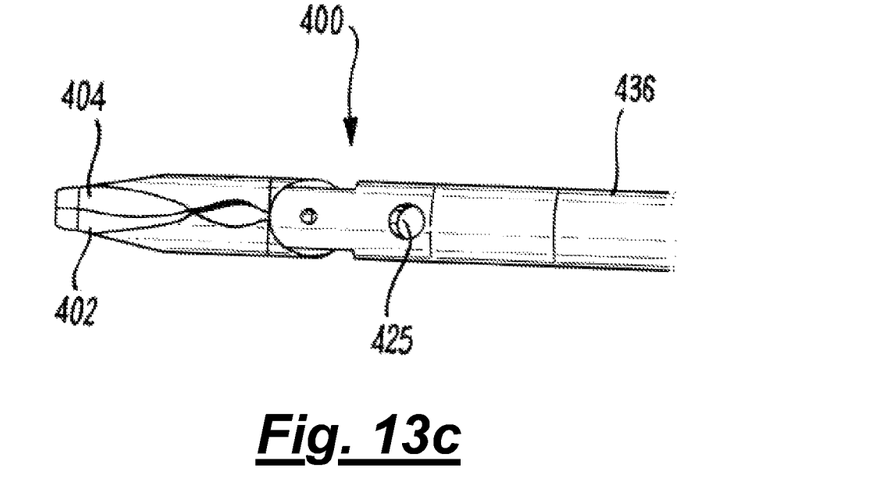
FIG. 13c is a drawing of the anchor and applicator of FIG. 13a in a second position.

Referring to FIGS. 13a, b and c, in use, the attachment aperture 422 is attached to attachment means 426 of an applicator 428 for remotely operating the anchor 400. The attachment means 426 may be, for example, a hook which, in use, is passed through the attachment aperture of the anchor 400 to provide operational communication between the applicator and the jaws 402 and 404 of the anchor.

Referring to FIG. 13a, the applicator has a distal end 430 and a proximate end 432, the proximate end 432 being the end closest to the surgeon when the applicator is in use. The applicator 428 is shown in FIG. 13a in a broken length. However, it will be appreciated that, in use, the applicator 428 is of a length which is suitable for undertaking the surgical procedure.

The attachment means 426 is disposed on the distal end 430. At the proximate end 432 is an actuator 434 for remotely controlling the position of the attachment means 426. An actuator rod 436 extends from the attachment means 426 to an actuator handle 438 whereby the actuator handle 438 is operable, by pushing/pulling action, to move the actuator rod 436 in the direction of the longitudinal axis 440 of the applicator 428. An outer tube 437 extends along the length of the actuator rod 436 to provide protection.

As mentioned above, the anchor 400 is normally biased with its jaws, 402 and 404, closed and a force is required to open them.

In use, the anchor 400 is attached to the applicator 428 by way of the attachment means, 422 and 426, respectively. With the anchor and applicator attached to each other the anchor 400 is inserted into the surgical cavity of the patient through an incision. The jaws 402 and 404, of the anchor, are suitably positioned adjacent the tissue to which the anchor is to be attached. The actuator handle 438 is pulled which retracts the actuator member 436 towards the proximate end of the applicator 428 and thereby pulls the spring pin 420. Pulling the spring pin 420 back, pulls back the link joint 418 against the bias of the spring 419 and thereby opens the jaws 402 and 404. At this point in the procedure the jaws are open but the spring 419 maintains a biasing force to close the jaws.

With the jaws 402 and 404 open they are moved into position whereby the tissue to which the anchor is to be attached is disposed between them. The actuator handle 438 is then released in a controlled manner and the actuator member 436 is pulled forward as the spring 419 extends thereby clamping the jaws 402 and 404 closed onto the tissue. As the jaws are clamped closed the needle 412 pierces through the tissue and into the receiving hole 414 and the profiled facing surfaces 408 and 410 provide a seal around the incision made by the needle to prevent the leakage of fluids. The jaws 402 and 404 are held in the clamped position by the biasing force of the spring 419.

Once the anchor 400 has been attached to the tissue the applicator 428 can be released by removing the attachment hook 426 from the attachment aperture 422.

Referring to FIG. 13b, the applicator attachment means 426 is shown extended from the actuator member 436 to engage with the anchor attachment means 422. As shown in FIG. 13c, the applicator attachment means 426 is then withdrawn into the actuator member 436, which holds the anchor 400 in abutment against the end of the applicator 428.

Figure 14:
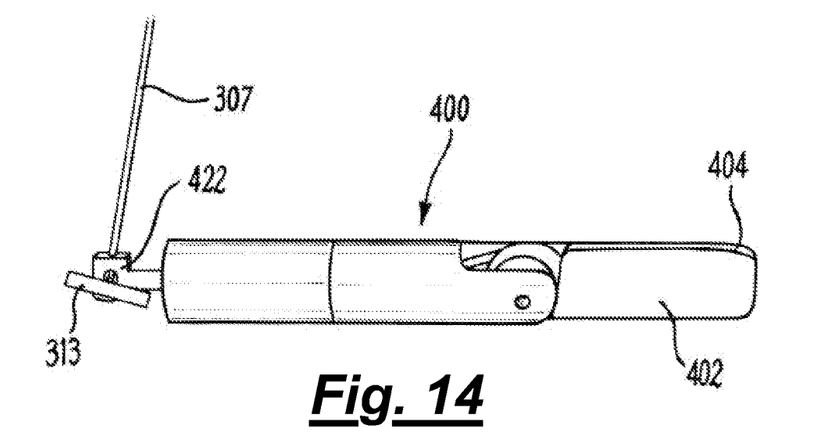
FIG. 14 is a drawing showing the surgical tissue anchor in a clamped state with a tether attached.

Referring to FIG. 14, with the anchor 400 attached to the tissue and the applicator 428 removed, a tether 307 can be attached to the anchor 400 through the attachment aperture 422. The tether 307 is attached to the anchor 400 by passing the tag 313 through the attachment aperture 422. This is undertaken by passing the end of the guide 311 (see FIGS. 8 and 10) through the attachment aperture 422 and withdrawing the guide back through the aperture 422 such that the tag 313 is left attached.

Figure 15:
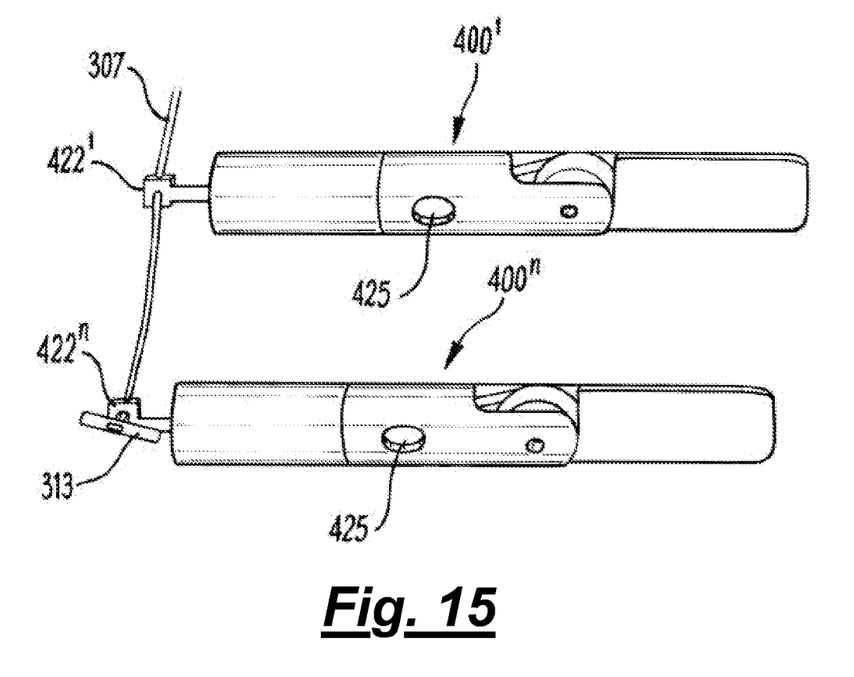
FIG. 15 is a drawing showing two surgical tissue anchors in a clamped state with a single tether attached to both anchors.

Referring also to FIG. 15, one or more additional anchors, $400^1$ to $400^n$, can be attached to the tether 307 in the same manner—i.e. by threading the guide 311 through the respective attachment apertures, $422^1$ to $422^n$ before withdrawing it to leave the tag 313 attached to the last threaded anchor.

Alternatively, or additionally, a tether 307 may be attached to an anchor 400 through the attachment aperture 425.

It is to be understood that the foregoing is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "e.g.," "for instance," "such as," and "like," and the verbs "comprising," "having," "including," and their other verb forms, when used in conjunction with a listing of one or more components or other items, are each to be construed as open-ended, meaning that that the listing is not to be considered as excluding other, additional components or items. Other terms are to be construed using their broadest reasonable meaning unless they are used in a context that requires a different interpretation.

The invention claimed is:

1. A surgical tissue anchor comprising:
  a plurality of jaws suitable for clamping onto tissue,
  clamping means operable to bias the jaws into a normally closed state, and
  attachment means operable for attachment of the anchor to one or more tethers for retracting the clamped tissue, wherein
  a first jaw of the plurality of jaws comprises a first facing surface, and a second jaw of the plurality of jaws comprises a second facing surface,
  the first facing surface has tissue piercing means extending therefrom towards the second facing surface, and the second facing surface has a receiving hole disposed suitably therein to receive the tissue piercing means when the jaws are in the normally closed state,
  the first facing surface and the second facing surface are profiled to cooperate with each other, in the normally closed state, to provide a seal therebetween,
  the tissue piercing means is curved,
  the attachment means comprises a mechanical actuator attachment aperture, extending through a mechanical actuator, and a pair of diametrically opposed housing apertures, extending through a covering housing, and
  the mechanical actuator attachment aperture and one of the diametrically opposed housing apertures are axially aligned to form a single attachment aperture.

2. A surgical tissue anchor as claimed in claim 1, wherein the tissue piercing means is a needle.

3. A surgical tissue anchor as claimed in claim 1, wherein the clamping means comprises a biasing spring operable to provide a biasing force on the jaws to urge the jaws into the normally closed state.

4. A surgical tissue anchor as claimed in claim 1, wherein the mechanical actuator comprises a spring pin and is operable to translate a force applied to the spring pin, substantially in a direction of a longitudinal axis thereof, into a force to separate the jaws.

5. A surgical tissue anchor as claimed in claim 4, wherein the attachment means is disposed on the spring pin.

6. A surgical tissue anchor as claimed in claim 5, wherein the attachment means is disposed on a peripheral portion of the spring pin.

7. A surgical tissue anchor as claimed in claim 1, wherein the mechanical actuator attachment aperture is oval in shape.

8. A surgical tissue anchor as claimed in claim 1, further comprising an applicator for remotely clamping the anchor to tissue.

9. A surgical tissue anchor as claimed in claim 8, wherein the applicator comprises attachment means operable to detachably attach the applicator to the attachment means of the anchor.

10. A surgical tissue anchor as claimed in claim 9, wherein the attachment means of the applicator comprises a hook-shaped connector.

11. A surgical tissue anchor as claimed in claim 8, wherein the applicator comprises an actuator rod connected to an actuator handle, the actuator handle being operable to move the actuator rod in a direction along its longitudinal axis.

12. A surgical tissue anchor as claimed in claim 11, wherein movement of the actuator rod in the direction along its longitudinal axis causes the jaws of the anchor to separate.

13. A surgical tissue anchor as claimed in claim 1,
wherein the tissue piercing means has a length at least two times greater than its diameter.

14. A surgical tethering and retraction kit comprising a surgical guide and one or more surgical tissue anchors,
said one or more surgical tissue anchors comprising:
a plurality of jaws suitable for clamping onto tissue,
clamping means operable to bias the jaws into a normally closed state, and attachment means operable for attachment of the anchor to one or more tethers for retracting the clamped tissue, wherein
a first jaw of the plurality of jaws comprises a first facing surface, and a second jaw of the plurality of jaws comprises a second facing surface,
the first facing surface has tissue piercing means extending therefrom towards the second facing surface, and the second facing surface has a receiving hole disposed suitably therein to receive the tissue piercing means when the jaws are in the normally closed state,
the first facing surface and the second facing surface are profiled to cooperate with each other, in the normally closed state, to provide a seal therebetween,
the tissue piercing means is curved,
the surgical guide comprises a handle portion, a needle extending from the handle portion, and a tether, and
the tether comprises an attachment tag disposed thereon.

15. A surgical kit as claimed in claim 14, wherein the needle is adjustable in length.

16. A surgical kit as claimed in claim 15, wherein the needle is telescopic.

17. A surgical kit as claimed in claim 14, wherein the surgical guide further comprises a tether clamp operable to clamp the tether at a desired length.

18. A surgical kit as claimed in claim 17, wherein the tether clamp is a spring biased clamp.

19. A surgical kit as claimed in claim 17, wherein the tether clamp is a screw clamp.

20. A surgical kit as claimed in claim 14, wherein the surgical guide further comprises an inner sleeve disposed within the needle coaxially therewith.

21. A surgical kit as claimed in claim 20, wherein the inner sleeve is extendible in the direction of its longitudinal axis such that the inner sleeve is capable of being exposed beyond a distal end of the needle.

22. A surgical kit as claimed in claim 14, wherein the surgical guide further comprises a retaining flange suitably disposed and operable to rest on the skin of an animal or a human body and thereby cover an incision through which the guide extends.

23. A surgical tethering and retraction kit comprising a surgical guide and one or more surgical tissue anchors, said one or more surgical tissue anchors comprising:
a plurality of jaws suitable for clamping onto tissue,
clamping means operable to bias the jaws into a normally closed state, and attachment means operable for attachment of the anchor to one or more tethers for retracting the clamped tissue, wherein
a first jaw of the plurality of jaws comprises a first facing surface, and a second jaw of the plurality of jaws comprises a second facing surface,
the first facing surface has tissue piercing means extending therefrom towards the second facing surface, and the second facing surface has a receiving hole disposed suitably therein to receive the tissue piercing means when the jaws are in the normally closed state,
the first facing surface and the second facing surface are profiled to cooperate with each other, in the normally closed state, to provide a seal therebetween,
the tissue piercing means is curved,
the surgical guide comprises a handle portion, a tubular guide extending from the handle portion, an inner sleeve disposed within the tubular guide coaxially therewith,
the inner sleeve is biased by a spring attached thereto, the spring being disposed in the handle portion and a tether, and
the tether comprises an attachment tag disposed thereon.

24. A surgical tethering and retraction kit comprising a surgical guide and one or more surgical tissue anchors, said one or more surgical tissue anchors comprising:
a plurality of jaws suitable for clamping onto tissue,
clamping means operable to bias the jaws into a normally closed state, and attachment means operable for attachment of the anchor to one or more tethers for retracting the clamped tissue, wherein
a first jaw of the plurality of jaws comprises a first facing surface, and a second jaw of the plurality of jaws comprises a second facing surface,
the first facing surface has tissue piercing means extending therefrom towards the second facing surface, and the second facing surface has a receiving hole disposed suitably therein to receive the tissue piercing means when the jaws are in the normally closed state,
the first facing surface and the second facing surface are profiled to cooperate with each other, in the normally closed state, to provide a seal therebetween,
the tissue piercing means is curved,
the surgical guide comprises a handle portion, a tubular guide extending from the handle portion, an inner sleeve disposed within the tubular guide coaxially therewith, and a tether,
the tether comprises an attachment tag disposed thereon, and the inner sleeve comprises an aperture disposed at, or adjacent to, its distal end, through which the tether is capable of being extended.

* * * * *